(12) United States Patent
Pflaum

(10) Patent No.: US 6,198,790 B1
(45) Date of Patent: Mar. 6, 2001

(54) X-RAY DIAGNOSTIC APPARATUS INCLUDING A CT SYSTEM AND A SYSTEM FOR PRODUCING RADIOGRAPHS

(75) Inventor: Michael Pflaum, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/235,183

(22) Filed: Jan. 22, 1999

(30) Foreign Application Priority Data

Jan. 22, 1998 (DE) .............................. 198 02 405

(51) Int. Cl.[7] .................................................. A61B 6/00
(52) U.S. Cl. ..................... 378/9; 378/92; 378/4
(58) Field of Search ....................... 378/9, 92, 4

(56) References Cited

U.S. PATENT DOCUMENTS

| 5,068,882 | * | 11/1991 | Eberhard | .................................. | 378/4 |
| 5,293,416 | | 3/1994 | Pfeiler . | | |
| 5,485,494 | * | 1/1996 | Williams et al. | ....................... | 378/16 |
| 5,604,778 | * | 2/1997 | Polacin et al. | ............................. | 378/4 |
| 5,966,422 | * | 10/1999 | Dafni et al. | ................................ | 378/9 |

FOREIGN PATENT DOCUMENTS 295 21 308 U    2/1997 (DE) .

\* cited by examiner

*Primary Examiner*—David V. Bruce
*Assistant Examiner*—Pamela R. Hobden
(74) *Attorney, Agent, or Firm*—Schiff Hardin & Waite

(57) ABSTRACT

An X-ray diagnostic apparatus has a computed tomography device including a first X-ray tube, which is fastened to a gantry ring (10) and which emits a fan-shaped effective beam, and an opposed radiation receiver, which is formed by a row of individual detectors, each of which forms an electrical signal corresponding to the received radiation intensity. A second X-ray tube is additionally fastened to the gantry ring at a right angle to the first X-ray tube, opposite which, at the gantry ring, a matrix-like X-ray detector is arranged. The second X-ray tube is activated in specified positions in pulsed fashion, such as at the uppermost rotational point. X-ray shadowgraphs thus can be produced simultaneously with CT images and without a need for repositioning any of the apparatus components.

8 Claims, 2 Drawing Sheets

X-RAY DIAGNOSTIC APPARATUS INCLUDING A CT SYSTEM AND A SYSTEM FOR PRODUCING RADIOGRAPHS

BACKGROUND OF THE INVENTION

1. Field of the Invention

The present invention relates to an X-ray diagnostic apparatus with a computed tomography device of the type having an X-ray tube, which is fastened to a gantry ring and which emits a fan-shaped effective beam, and an opposed radiation receiver, which consists of a row of single detectors, each of which forms an electrical signal corresponding to the received radiation intensity.

2. Description of the Prior Art

German Utility Model 295 21 308 discloses an X-ray examination system with a computed tomography device and other receiving devices relevant to X-ray technology in which components of the system can be used jointly in connection with the computed tomography device and the other receiving devices.

In a computed tomography device of this type, an image of the irradiated slice of the examination subject is reconstructed from the output signals of the individual detectors obtained at various irradiation directions. Digital radiographs can also be generated in a shadow-image mode by the additionally provided X-ray device. To do this, however, the gantry of the computed tomography device must be pushed to the side so that the image pick-up by the additional X-ray device can proceed undisturbed.

U.S. Pat. No. 5,293,416 describes a computed tomography device with a curved CT detector in which an additional, stationary detector array for the creation of X-ray shadow images is provided. This additional detector array is arranged perpendicularly to the plane formed by the curved CT detector, i.e., it is arranged in the direction of the axis of rotation of the X-ray tube. A diaphragm which directs a fan-shaped X-ray onto the detector array for every position of the X-ray tube is provided in the beam path. CT exposures and X-ray shadow images can not occur simultaneously in this apparatus either, since at least the diaphragm must be pushed into the beam path of the X-ray tube.

U.S. Pat. No. 5,604,778 teaches a computed tomography device for spiral scanning which has a number of X-ray tubes, which are attached to the gantry ring, and a stationary annular CT detector row, or a number of CT detector rows which are fastened to the gantry ring, so that an improved and faster spiral scanning can occur. X-ray shadow images can not be produced with this apparatus.

SUMMARY OF THE INVENTION

It is an object of the present invention to provide a computed tomography apparatus of the abovementioned type wherein X-ray images can be easily created together with CT slice exposures.

This object is achieved in an X-ray diagnostic apparatus according to the invention wherein a second X-ray tube is fastened to the gantry ring, opposite which a matrix-shaped X-ray detector is arranged at the gantry ring, the second X-ray tube being activated in specific positions in a pulse-like fashion. It is thus possible that low-power X-ray exposures can be created simultaneously with the acquisition of the measurement values for the production of the slice exposures.

It has proven advantageous to fasten the second X-ray tube to the gantry ring at a right angle to the first X-ray tube.

In order to register topograms, the second X-ray tube is activated when it is a uppermost point (top dead center) during a rotation of the gantry ring.

Biplanar exposures can be created when the second X-ray tube is activated, in pulse-like fashion, not only at the uppermost point, but also at a point which is rotationally shifted 90° relative to top dead center.

Image pairs can be inventively picked up in an X-ray stereo made wherein the second X-ray tube is activated in pulse-like fashion at a specific angle of rotation before the uppermost point and at the same angle of rotation after the uppermost point. This angle of rotation can be 30°, for example.

A phase shifter can be connected upstream to the high-voltage generator for the second X-ray tube, this phase shifter being constructed to shift the activation point of the second X-ray tube with respect to the uppermost point.

A precise triggering of the X-ray pulse is accomplished in an embodiment wherein a position detector is allocated to the gantry ring, this position detector being connected to a control unit which effects the pulsed activation of the high-voltage generator for the second X-ray tube.

DESCRIPTION OF THE PREFERRED EMBODIMENTS

Figure 1:
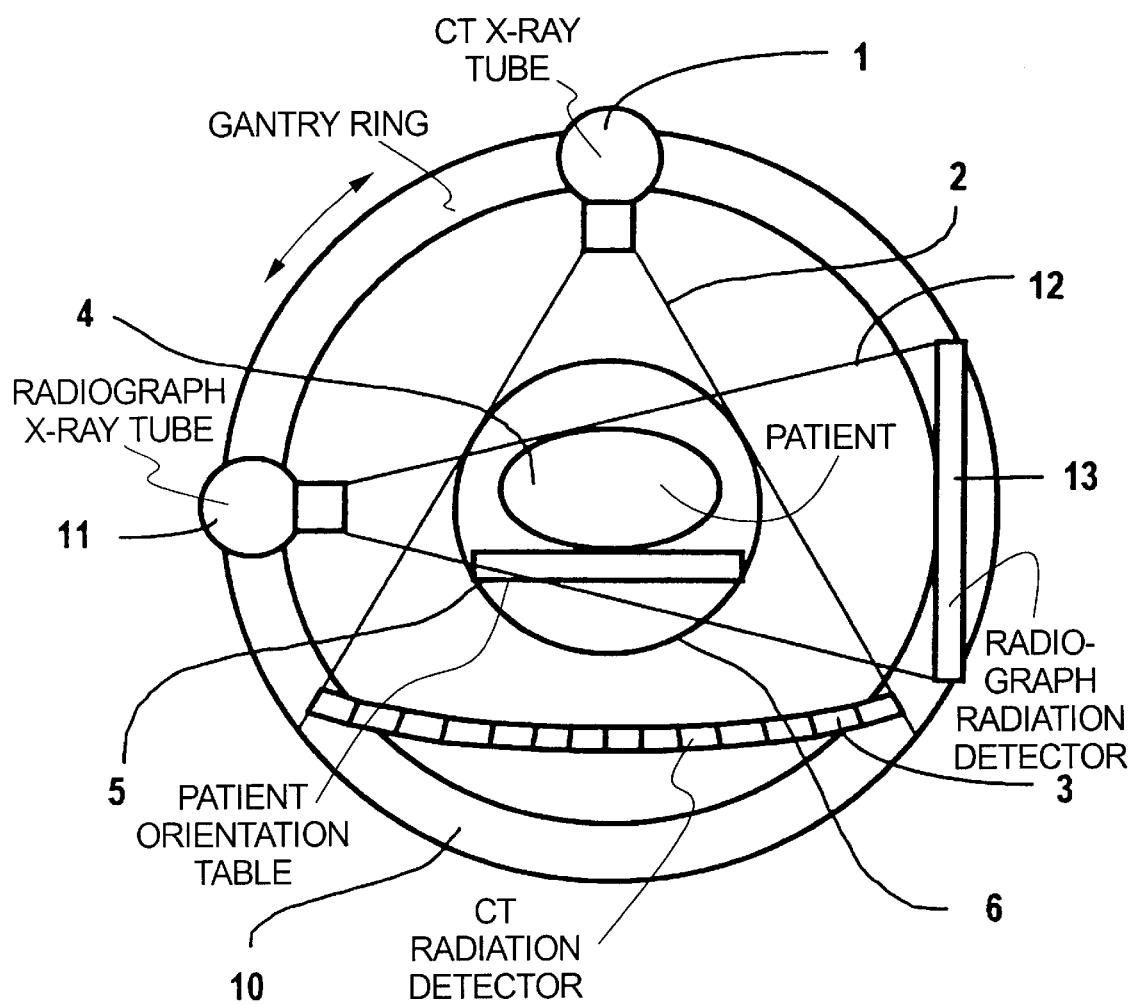
FIG. 1 is a schematic illustration of an inventive X-ray diagnostic apparatus with a computed tomography device.

The computed tomography device of the X-ray diagnostic apparatus according to FIG. 1 has a measuring unit which includes a first X-ray source 1, which emits a fan-shaped first X-ray beam 2, and a radiation receiver 3, which consists of a row of individual detectors—512 individual detectors, for instance. The patient 4 to be examined lies on a patient orientation table 5. For scanning the patient 4, the measuring unit is rotated through 360° around a measuring field 6 in which the patient 4 lies.

Figure 2:
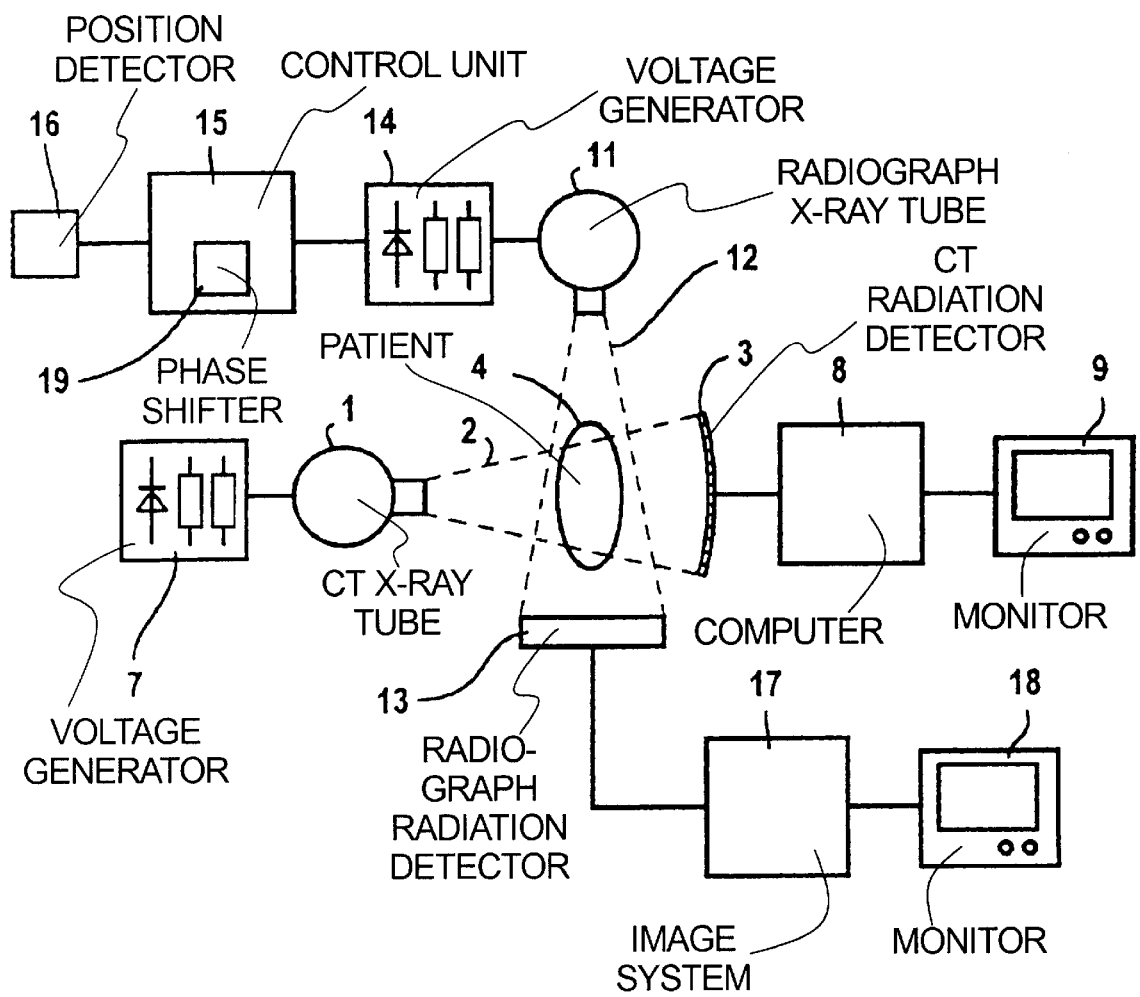
FIG. 2 is a block diagram showing the basic electrical components of the inventive X-ray diagnostic apparatus of FIG. 1.

The X-ray source 1, which is powered by a first voltage generator 7, which is depicted in FIG. 2, is pulsed or operated to emit continuous radiation. In specified angle positions of the measuring unit sets of data are generated which are fed to a computer 8 by the radiation receiver 3. The computer 8, in a known manner, calculates the coefficients of attenuation of specified image points and reproduces these on a monitor 9. An image of the irradiated slice of the patient 4 appears on the monitor 9.

The different irradiation directions (projection angles) of the effective beam 2 are produced by rotation, by means of a rotation apparatus (not depicted), of a gantry ring 10 to which the X-ray source 1 and the radiation receiver 3 are attached.

A second X-ray source 11, which is offset 90° relative to the first X-ray source 1, is also attached to the gantry ring 10. This second X-ray source 11 emits a second X-ray beam 12, which strikes a flat X-ray detector 13 which is attached at the opposite side of the gantry ring 10. The X-ray detector 13 comprises a number of pixels arranged in a matrix in known fashion. For example, the detector 13 can be a solid-state image converter made of amorphous silicon (aSi:H) which converts the X-ray image into electrical signals directly or following a conversion of the incident X-rays into a visible image by a scintillator.

The second X-ray source 11 is powered by a second voltage generator 14 which is operated in pulsed fashion by a control unit 15. A position detector 16 is connected to the control unit 15, the detector 16 delivering a signal to the control unit 15 corresponding to the angle of rotation of the gantry ring 10. On the basis of this angle information from the position detector 16, the control unit 15 identifies the location of the second X-ray source 11 and activates the second X-ray source 11 accordingly, as previously explained.

The solid-state image converter 13 is connected to a digital image system 17, to which a second monitor 18 for the reproduction of an X-ray image is connected. The digital image system 17 can include processing circuits, converters, differential circuits and image memories in known fashion.

If the gantry ring 10 is operated continuously for normal CT examination, then a flat X-ray image can be simultaneously generated by the X-ray imaging system formed by the second X-ray source 11 and the detector 13. To this end, as controlled via the position detector 16, the second X-ray source 11 is activated when the second X-ray source 11 is located at the uppermost point of rotation. This can be designated as normal operation, wherein low-power exposures—known as topograms—are generated, for example.

A mode of operation known as biplanar imaging can also be enabled with such an inventive X-ray diagnostic apparatus by operating the second X-ray tube 11 in pulsed fashion, not only in the uppermost point but also at a point offset therefrom by 90°. Both frontal and lateral surface exposures are thereby generated. The position detector 16 can also detect this second, offset position and supply a signal to the control unit 15. Alternatively a phase shifter 19 can be provided in the control unit 15, the phase shifter 19 effecting a shifting of the control pulses such that the second X-ray source 11 is first triggered at a 90° position. Since gantry ring 10 of the CT measuring unit performs repeated rotations, it is not necessary for an X-ray image to be generated in each rotation. Thus, for example, in the first rotation, of the second X-ray source 11 activation can occur at the uppermost point, while in the second rotation, the activation of the second X-ray source 11 ensues at the 90° angle. There can also be a larger time interval between the individual exposures, however, so that there is enough time for a readout of the solid-state image converter.

Stereo exposures can also be produced with such an X-ray diagnostic apparatus by operating the second X-ray tube 11 such that X-ray exposures are generated shortly before and shortly after the uppermost point, respectively. The magnitude of the respective angles of rotation of the activation positions can be identical, such as 30°, for example.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray diagnostic apparatus comprising:
   a computed tomography system having a rotatable gantry ring with a first X-ray tube mounted on said gantry ring and a radiation receiver mounted on said gantry ring opposite said first X-ray tube, said radiation receiver emitting electrical signals dependent on attenuated X-rays incident thereon, and a computer supplied with said electrical signals for reconstructing a tomographic image therefrom, said computed tomography system being continuously operated as said gantry ring rotates; and
   a system for producing a radiographic image independently of said computed tomographic system, including a second X-ray tube mounted on said gantry ring and a matrix-like radiation detector mounted on said gantry ring opposite said second X-ray source, and a control unit connected to said second X-ray tube for activating said second X-ray tube in pulsed fashion only at predetermined rotational positions of said second X-ray tube as said gantry ring rotates.

2. An X-ray diagnostic apparatus as claimed in claim 1 wherein said second X-ray tube is mounted on said gantry ring at 90° from said first X-ray tube.

3. An X-ray diagnostic apparatus as claimed in claim 1 wherein said second X-ray tube periodically assumes an uppermost point of rotation as said gantry ring rotates, and wherein said control unit activates said second X-ray tube at said uppermost point.

4. An X-ray diagnostic apparatus as claimed in claim 1 wherein said control unit also activates said second X-ray tube at a position of said second X-ray tube which is 90° from said uppermost point as said gantry ring rotates.

5. An X-ray diagnostic apparatus as claimed in claim 1 wherein said second X-ray tube assumes an uppermost point of rotation as said gantry ring rotates, and wherein said control unit activates said second X-ray tube at a first predetermined angle preceding said uppermost point and at a second predetermined angle, equal to said first predetermined angle, following said uppermost point.

6. An X-ray diagnostic apparatus as claimed in claim 5 wherein said first predetermined angle and said second predetermined angle each equal 30°.

7. An X-ray diagnostic apparatus as claimed in claim 1 wherein said second X-ray tube assumes an uppermost point of rotation as said gantry ring rotates, and wherein said system for producing a radiographic image further comprises a phase shifter connected between said control unit and said second X-ray tube, said phase shifter shifting activation of said second X-ray tube to a point in time at which said second X-ray tube assumes a predetermined angular position relative to said uppermost point of rotation.

8. An X-ray diagnostic apparatus as claimed in claim 1 wherein said system for producing a radiographic image further comprises a position detector which generates a signal identifying an angular position of said second X-ray tube as said gantry ring rotates, said position detector supplying said signal to said control unit and said control unit activating said second X-ray tube when said signal indicates said second X-ray tube is at a predetermined angular position.

* * * * *